United States Patent
Connolly et al.

(10) Patent No.: US 6,864,244 B2
(45) Date of Patent: Mar. 8, 2005

(54) ANHYDROUS CRYSTALLINE 1-[4(S)-AZIDO-2(S), 3(R)-DIHYDROXY-4-(HYDROXYMETHYL)-1(R)-CYCLOPENTYL]CYTOSINE HEMISULFATE AS USEFUL AS AN ANTIVIRAL AGENT

(75) Inventors: Terrence Joseph Connolly, Redwood City, CA (US); Joseph Armstrong Martin, Menlo Park, CA (US); Anthony Prince, Los Altos, CA (US); Keshab Sarma, Sunnyvale, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 10/731,582

(22) Filed: Dec. 9, 2003

(65) Prior Publication Data

US 2004/0162265 A1 Aug. 19, 2004

Related U.S. Application Data

(60) Provisional application No. 60/431,885, filed on Dec. 9, 2002.

(51) Int. Cl.[7] ............... A61K 31/7068; A61K 31/7052; A61K 31/70; C07H 19/067
(52) U.S. Cl. .................. 514/49; 514/934; 514/894; 536/28.51; 536/28.5; 536/55.3
(58) Field of Search .................. 514/49, 934, 894; 536/28.51, 28.5, 55.3

(56) References Cited

U.S. PATENT DOCUMENTS 5,449,664 A * 9/1995 Verheyden et al. ........... 514/45

FOREIGN PATENT DOCUMENTS

WO   WO 02/18404 A2 * 3/2002
WO   WO 02/100415 A2 * 12/2002

OTHER PUBLICATIONS

Moffatt, J.G., "Chemical Transformations of the Sugar Moiety of Nucleosides", Nucleoside Analogues, (R. T. Walker, E. De Clercq, & F. Eckstein, eds.), (1979), pp. 71–164, Plenum Press, New York. (see p. 144).

Maag, Hans, et al., "Synthesis and Anti–HIV Activity of 4′–Azido– and 4′– Methoxynucleosides," *J. Med. Chem.*, 1992, pp. 1440–1451, 35(8), (Table I).

* cited by examiner

*Primary Examiner*—James O. Wilson
*Assistant Examiner*—Michael C. Henry
(74) *Attorney, Agent, or Firm*—Brian L. Buckwalter

(57) ABSTRACT

The present invention relates to the hemisulfate salt of 1-[4(S)-azido-2(S),3(R)-dihydroxy-4-(hydroxymethyl)-1(R)-cyclopentyl]cytosine (Ia) with improved stability and physical properties which facilitate manufacturing, handling and formulating I and polymorphic crystalline forms thereof.

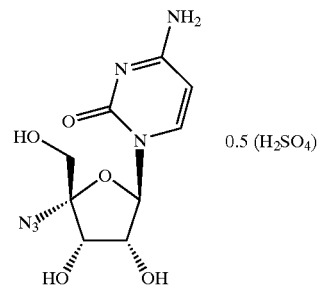

(Ia)

20 Claims, 5 Drawing Sheets

ANHYDROUS CRYSTALLINE 1-[4(S)-AZIDO-2(S), 3(R)-DIHYDROXY-4-(HYDROXYMETHYL)-1(R)-CYCLOPENTYL]CYTOSINE HEMISULFATE AS USEFUL AS AN ANTIVIRAL AGENT

CROSS REFERENCE TO PRIOR APPLICATION

This application claims benefit under Title 35 U.S.C. 119(e) of U.S. Provisional Application No. 60/431,885, filed Dec. 9, 2002, which is hereby incorporated by reference in its entirety.

FIELD OF THE INVENTION

The present invention relates to the hemisulfate salt of 1-[4(S)-azido-2(S),3(R)-dihydroxy-4-(hydroxymethyl)-1(R)-cyclopentyl]cytosine Ia with improved stability and physical properties which facilitate manufacturing, handling and formulating I and polymorphic crystalline forms thereof.

BACKGROUND OF THE INVENTION

The compound 1-[4(S)-azido-2(S),3(R)-dihydroxy-4-(hydroxymethyl)-1(R)-cyclopentyl]cytosine I is a potent antiviral agent. (U.S. patent application Ser. No. 10/167,106 file Jun. 11, 2002; J. G. Moffatt, In *Nucleoside Analogs*; R. T. Walker, E. DeClercq and F. Eckstein, Eds., Plenum Publishing, New York, 1979, p144; H. Maag et al., *J. Med. Chem.* 1992 35:1440–1451). While biological activity is a sine non qua for an effective drug, the compound must be capable of large scale manufacturing and the physical properties of the compound can markedly impact the effectiveness and cost of a formulated active ingredient. Although it possesses potent antiviral activity, use of the free base I is limited by its thermal instability, poor crystallinity and hygroscopicity which create challenging handling and formulating problems.

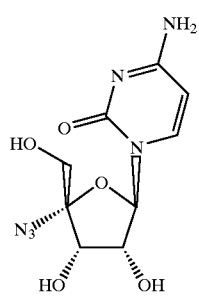

(I)

Salts of acidic and basic compounds can alter or improve the physical properties of a parent compound. These salt forming agents, however, must be identified empirically by the pharmaceutical chemist since there is no reliable method to predict the influence of a salt species on the behavior of a parent compound in dosage forms. Effective screening techniques, which potentially could simplify the selection process, are unfortunately absent (G. W. Radebaugh and L. J. Ravin Preformulation. In, *Remington: The Science and Practice of Pharmacy*; A. R. Gennaro Ed.; Mack Publishing Co. Easton, Pa., 1995; pp 1456–1457).

Different polymorphic forms of salts are frequently encountered among pharmaceutically useful compounds. Polymorphism is the ability of any element or compound to crystallize as more than one distinct crystalline species. Physical properties including solubility, melting point, density, hardness, crystalline shape and stability can be quite different for different polymorphic forms of the same chemical compound.

Polymorphic forms are characterized by scattering techniques, e.g., x-ray diffraction powder pattern, by spectroscopic methods, e.g., infa-red, $^{13}C$ nuclear magnetic resonance spectroscopy and by thermal techniques, e.g, differential scanning calorimetry or differential thermal analysis. The compound of this invention is best characterized by the X-ray powder diffraction pattern determined in accordance with procedures which are known in the art. For a discussion of these techniques see J. Haleblian, *J. Pharm. Sci.* 1975 64:1269–1288, and J. Haleblain and W. McCrone, *J. Pharm. Sci.* 1969 58:911–929. Although the intensities of peaks in the x-ray powder diffraction patterns of different batches of the hemisulfate Ia may vary slightly, the peaks and the peak locations are characteristic for a specific polymorphic form.

The problem which must be solved is to identify a suitable salt which (i) possesses adequate chemical stability during the manufacturing process, (ii) is efficiently prepared, purified and recovered, (ii) provides acceptable solubility in pharmaceutically acceptable solvents, (iii) is amenable to manipulation (e.g. flowability and particle size) and formulation with negligible decomposition or change of the physical and chemical characteristics of the compound, (iv) exhibits acceptable chemical stability in the formulation. In addition, salts containing a high molar percent of the active ingredient are highly desireable since they minimize the quantity of material which must be formulated and administered to produce a therapeutically effective dose. These often conflicting requirements make identification suitable salts a challenging and important problem which must be solved by the skilled pharmaceutical scientist before drug development can proceed in earnest.

SUMMARY OF THE INVENTION

This invention relates to hemisulfate crystalline forms of 1-[4(S)-azido-2(S),3(R)-dihydroxy-4-(hydroxymethyl)-1(R)-cyclopentyl]cytosine (Ia), methods to prepare polymorphic crystalline

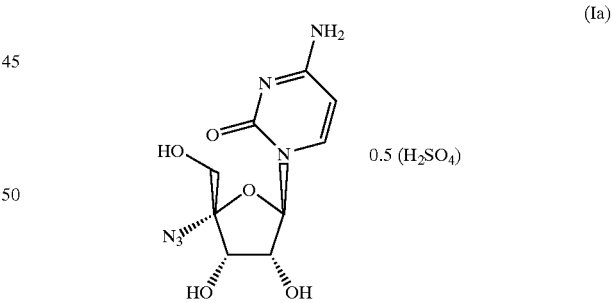

(Ia)

forms of (Ia), pharmaceutical compositions containing the hemisulfate salt (Ia), and methods to treat diseases mediated by the Hepatitis C Virus using hemisulfate salt (Ia).

BRIEF DESCRIPTION OF THE FIGURES

The numerous objects and advantages of the present invention can be directly understood by those skilled in the art by reference to the accompanying figure in which.

DETAILED DESCRIPTION OF THE INVENTION

Surprisingly, the hemisulfate of I has been found to be significantly more stable than the free base and, in addition, it is an anhydrous non-hygroscopic crystalline salt with superior properties relative to other salts. Three new anhydrous polymorphic forms, Form A, Form B and Form C, of the hemisulfate salt of I have been isolated and identified. Form A and B are transformed into Form C in the present of moisture.

In one embodiment of the present invention there is provided a hemisulfate salt of 1-[4(S)-azido-2(S),3(R)-dihydroxy-4-(hydroxymethyl)-1(R)-cyclopentyl]cytosine (Ia) and solvates thereof.

Figure 1:
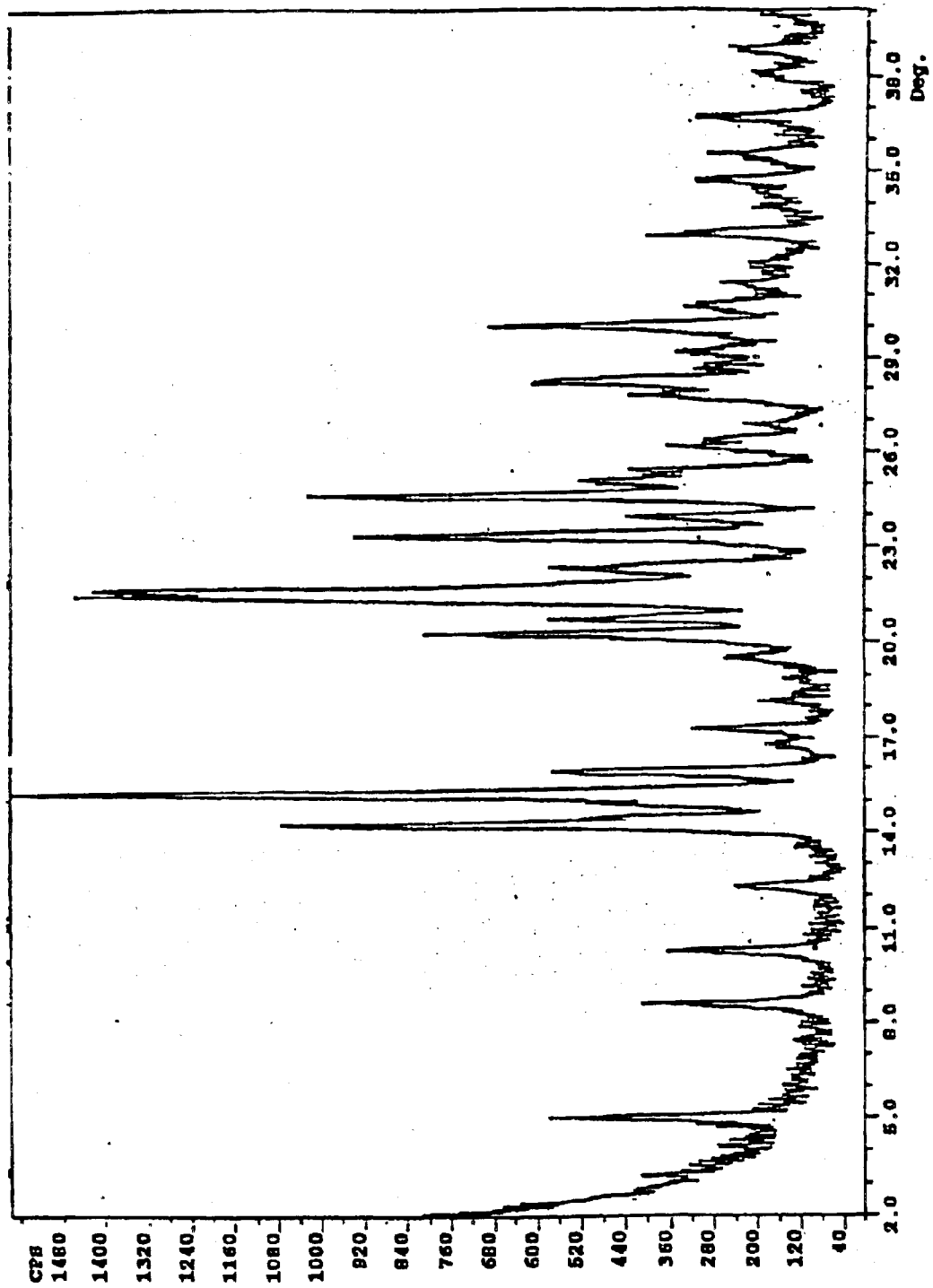
FIG. 1 shows the x-ray powder diffraction of the Form A polymorphic form of Ia.

In another embodiment of the present invention there is provided a polymorph crystalline form (Form A) of a compound according to claim 1 with an X-ray scattering pattern as shown in FIG. 1.

In another embodiment there is provided a process for preparing the Form A polymorphic crystalline form of Ia by crystallizing the compound (I) from an aged solution ethanol sulfuric acid.

Figure 2:
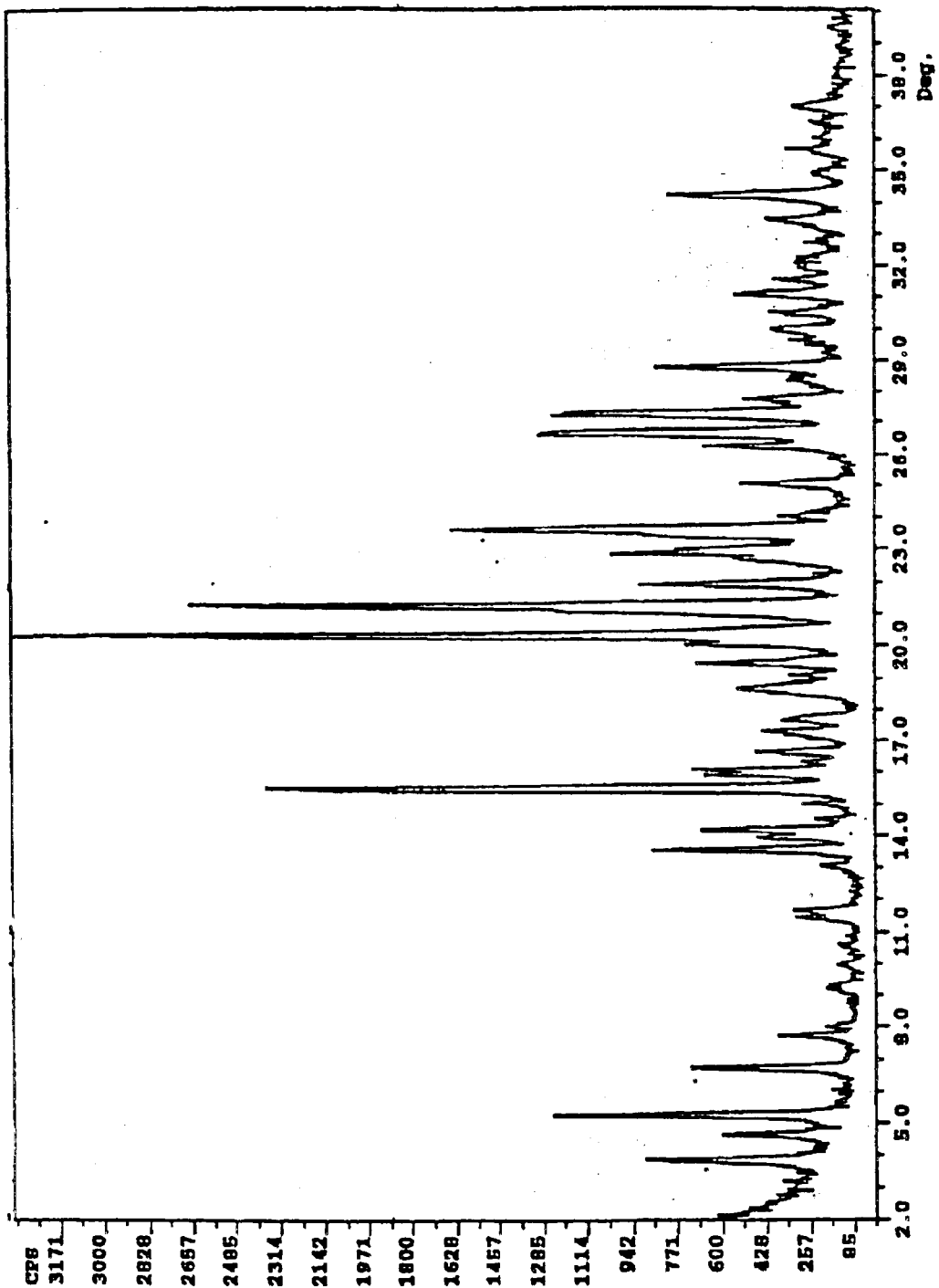
FIG. 2 shows the x-ray powder diffraction of the Form B polymorphic form of Ia.

In another embodiment of the present invention there is provided a polymorphic crystalline form of Ia (Form B) with an X-ray scattering pattern as shown in FIG. 2.

In another embodiment there is provided a process for preparing Form B polymorphic crystalline form of Ia by crystallizing (I) from isopropanol/water (85:15) and sulfuric acid.

Figure 3:
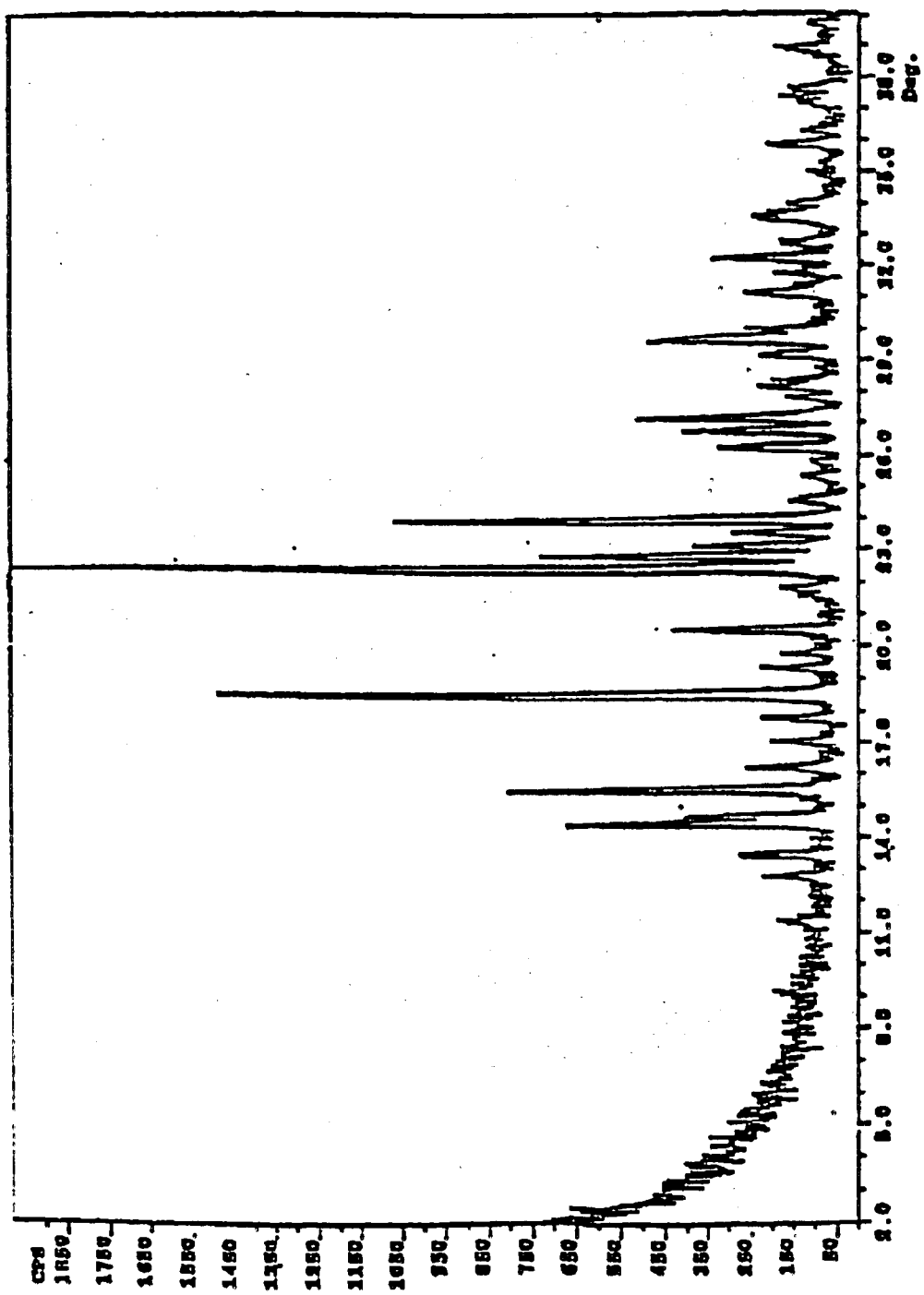
FIG. 3 shows the x-ray powder diffraction of the Form C polymorphic form of Ia.
Figure 4:
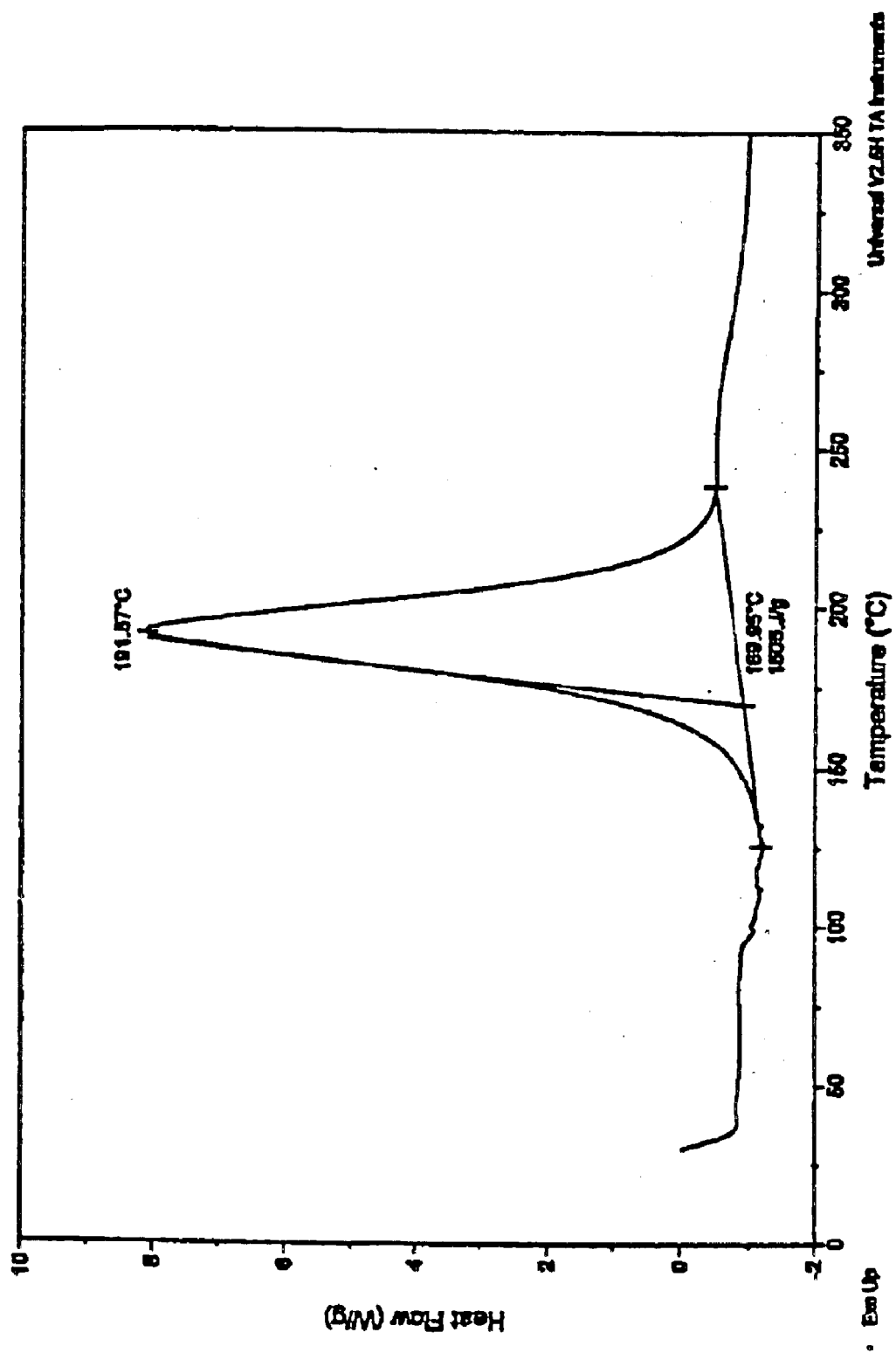
FIG. 4 show the differential scanning calorimetry curve for the free base I.
Figure 5:
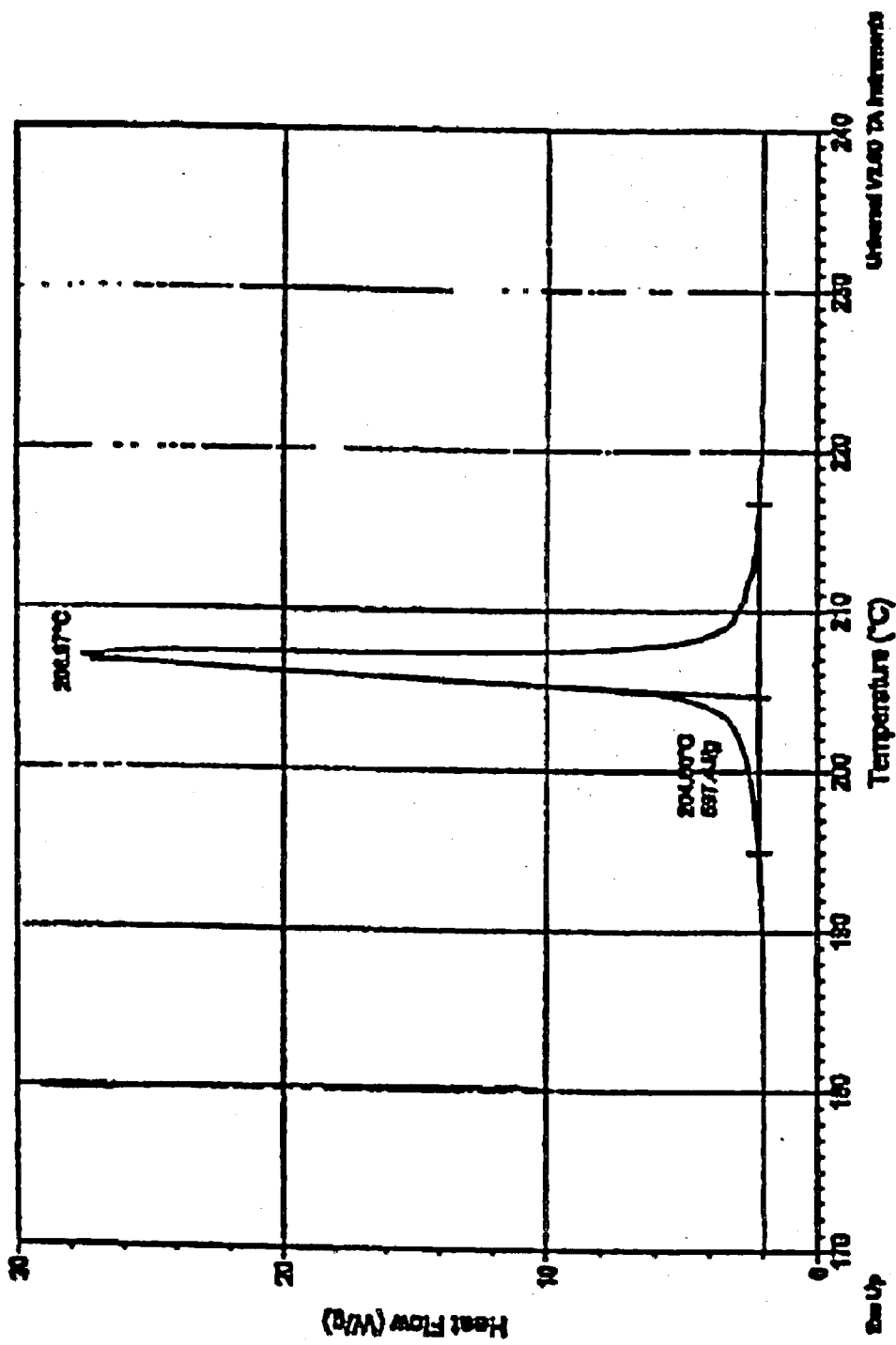
FIG. 5 show the differential scanning calorimetry curve for the Form C polymorphic crystalline form of Ia.

In another embodiment of the present invention there is provided a polymorphic crystalline form of Ia (Form C) with an X-ray diffraction pattern as shown in FIG. 3.

In another embodiment there is provided a process for preparing said Form C polymorphic crystalline form of Ia by crystallizing I from isopropanol/water (60:40) in the presence of sulfuric acid. In another embodiment of the present invention the isopropanol/water recrystallization solution is adjusted from a pH of about 5 to a pH of about 3 with sulfuric acid.

In another embodiment of the present invention there is provided a method for treating a disease mediated by Hepatitis C virus by administering to a patient in need thereof a therapeutically effective amount of compound of Form A polymorph of Ia.

In another embodiment of the present invention there is provided a method for treating a disease mediated by Hepatitis C virus by administering to a patient in need thereof a therapeutically effective amount of compound of Form B polymorph of Ia.

In another embodiment of the present invention there is provided a method for treating a disease mediated by Hepatitis C virus by administering to a patient in need thereof a therapeutically effective amount of compound of Form C polymorph of Ia.

In another embodiment of the present invention there is provided a method for treating a disease mediated by Hepatitis C virus by administering to a patient in need thereof a therapeutically effective amount of compound Ia delivered in a dose of between 1 and 100 mg/kg/body weight of the patient/day.

In another embodiment of the present invention there is provided a method for treating a disease mediated by Hepatitis C virus by administering to a patient in need thereof a therapeutically effective amount of compound Ia in combination with an immune system modulator.

In another embodiment of the present invention there is provided a method for treating a disease mediated by Hepatitis C virus by administering to a patient in need thereof a therapeutically effective amount of compound Ia in combination with an interferon or a chemically-derivatized interferon.

In another embodiment there is provided a pharmaceutical composition comprising the hemisulfate salt of I in admixture with at least one pharmaceutically acceptable carrier or excipient.

The nucleoside I is an organic azide which is potentially thermally unstable. Differential scanning calorimetry (DSC) of I defined no melt endotherm. A large exothermic decomposition peak was recorded, onset temperature approximately 150° C., peak heat rate at 198° C., with a recorded enthalpy of −1053 J/g.

All the polymorphic forms of the hemisulfate salt Ia exhibited better thermal stability than the parent compound I and various other salts. Differential scanning calorimetry of Form A of Ia exhibited an exothermic decomposition with onset at approximately 185° C. Form B of Ia exhibited exothermic decomposition onset at approximately 189° C. Form C of Ia exhibited exothermic decomposition onset at approximately 210° C.

Accelerating rate calorimetric (ARC) determination (adiabatic calorimetry conditions) of freebase I recorded a large decomposition exotherm with a corrected onset temperature of 102° C., Adiabatic Temperature Rise of 388° C. and an enthalpy of −194 Cal/g. The Form C of hemisulfate salt Ia, in contrast, exhibited a corrected exothermic decomposition onset temperature of 152° C., Adiabatic Temperature Rise of 265° C. and an enthalpy of −132 Cal/g, which substantially lessens the risks of decomposition during manufacture and processing.

The hemisulfate salts also provide improved physical properties and handling characteristics as shown in TABLE 1. No change in the chemical purity or polymophic form was observed when in accelerated stability tests at high temperature or high temperature and high relative humidity. The hemisulfate salt is a crystalline material with high bulk density which is more easily handled than the free base as evidenced by increased recoveries and improved flowability. The hemisulfate salt also has been found to be less hygroscopic than the free base. No weight gain was observed when Ia was stored at high relative humidity. Because of its non-hygroscopic nature anhydrous crystalline I hemisulfate retains a better physical appearance and handling properties over a longer period of time. An improvement in the physical appearance of a dosage form of a drug enhances both physician and patient acceptance and increases the likelihood of success of the treatment.

TABLE 1

Physical Properties of Form C Hemisulfate Ia

| CONDI-TIONS | TIME | APPEARANCE | WEIGHT GAIN | POLY-MORPH | ASSAY |
|---|---|---|---|---|---|
| 93% RH | 4 weeks | white powder | 0% | Form C | 99.9 |
| 60° C. | 1 week | white powder | N/A | Form C | 99.9 |
|  | 2 weeks | white powder | N/A | N/A | 99.9 |
|  | 4 weeks | white powder | N/A | Form C | 99.9 |
| 40° C./ | 1 week | white powder | N/A | Form C | 99.9 |
| 75% RH | 2 weeks | white powder | N/A | N/A | 99.9 |
|  | 4 weeks | white powder | N/A | Form C | 99.9 |

RH = Relative Humidity;
N/A = not assayed

The hemisulfate contributes little additional molecular weight of the active ingredient and the salt therefore has a high percentage of the parent compound minimizing the quantity of active ingredient which must be delivered to the patient. Since nucleosides frequently exhibit low bioavailabilty, this provides an additional advantage for the compounds of the present invention.

DEFINITIONS

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The term "hemisulfate" as used herein means a salt wherein there are two molar equivalents of the free base for each molar equivalent of sulfuric acid.

The term "solvate" as used herein means a compound of the invention or a salt, thereof, that further includes a stoichiometric or non-stoichiometric amount of a solvent bound by non-covalent intermolecular forces.

The term "hydrate" as used herein means a compound of the invention or a salt thereof, that further includes a stoichiometric or non-stoichiometric amount of water bound by non-covalent intermolecular forces. Hydrates are formed by the combination of one or more molecules of water with one of the substances in which the water retains its molecular state as $H_2O$, such combination being able to form one or more hydrate.

The term "clathrate" as used herein means a compound of the invention or a salt thereof in the form of a crystal lattice that contains spaces (e,g., channels) that have a guest molecule (e,g.), a solvent or water) trapped within.

The term "polymorphs" or "crystal forms" as used herein means crystal structures in which a compound can crystallize in different crystal packing arrangements, all of which have the same elemental composition. Different crystal forms usually have different X-ray diffraction patterns, infrared spectra, melting points, density hardness, crystal shape, optical and electrical properties, stability and solubility. Recrystallization solvent, rate of crystallization, storage temperature, and other factors may cause one crystal form to dominate.

The term "immunomodulator" as used herein means a therapeutic agent that assists in or is capable of modifying or regulating immune functions. An agent that causes an immunological adjustment, regulation or potentiation The term "interferon" as used herein means the family of proteins capable of interfering with the viral infection of cells, as well as inhibiting the proliferation of normal and transformed cells, regulating cell differentiation and modulating the immune system. The four major antigenic types of interferon ($\alpha,\beta,\gamma$ and $\omega$) are defined by the cellular source of their production. Type I interferons (interferon $\alpha,\beta$, and $\omega$) compete with each other for cellular binding to the type I interferon receptor and thus share at least some components of this multi-subunit cell surface receptor, while the receptor for type II interferon (interferon $\gamma$) is a distinct entity. Both naturally-occurring and recombinant interferons may be administered in combination therapy with compounds of the invention. A consensus sequence for interferon has been described in U.S. Pat. No. 4,897,471 (Y. Stabinsky).

The term "chemically-derivatized interferon" as used herein refers to an interferon molecule covalently linked to a polymer which alters the physical and/or pharmacokinetic properties of the interferon. A non-limiting list of such polymers include polyalkylene oxide homopolymers such as polyethylene glycol (PEG) or polypropylene glycol (PPG), polyoxyethylenated polyols, copolymers thereof and block copolymers thereof, provided that the water solubility of the block copolymers is maintained. One skilled in the art will be aware of numerous approaches to linking the polymer and interferon (for example, see A. Kozlowski and J. M. Harris *J. Control. Release* 2001 72(1–3):217–24; C. W. Gilbert and M. Park-Cho, U.S. Pat. No. 5,951,974). A non-limiting list of chemically derivatized IFN$\alpha$ contemplated in the present patent include PEG-interferon-$\alpha$-2a (PEGASYS®) and PEG-interferon-$\alpha$-2b (PEGINTRON™).

FORMULATIONS AND ADMINISTRATION

Formulations of compounds of formula I may be prepared by processes known in the formulation art. The following examples (infra) are given to enable those skilled in the art to more clearly understand and to practice the present invention. They should not be considered as limiting the scope of the invention, but merely as being illustrative and representative thereof.

The hemisulfate salts of the present invention can be administered in a variety of oral and parenteral dosage forms. Oral dosage forms can be tablets, coated tablets, dragées, hard and soft gelatin capsules, solutions, emulsions, syrups, or suspensions. Parenteral administration includes intravenous, intramuscular, intracutaneous, subcutaneous, intraduodenal, or intraperitoneal administration. Additionally, the salts of the present invention can be administered by transdermal (which may include a penetration enhancement agent), buccal, nasal and suppository routes. Also, the salts can be administered by inhalation.

For preparing pharmaceutical compositions from the compounds of the present invention, pharmaceutically acceptable carriers can be either solid or liquid. Solid form preparations include powders, tablets, pills, hard and soft gelatine capsules, cachets, dragées, suppositories, and dispersible granules. A solid carrier can be one or more substances which may also act as diluents, flavoring agents, solubilizers, lubricants, suspending agents, binders, preservatives, -tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired.

Suitable excipients for tablets, coated tablets, dragées, and hard gelatin capsules are, for example, lactose, corn starch and derivatives thereof, magnesium carbonate, magnesium stearate, sugar, lactose, pectin, dextrin, starch, gelatin, tragacanth, methylcellulose, sodium carboxymethylcellulose, talc, and fatty acids or their salts, e.g., stearic acid. If desired, the tablets or capsules may be enteric-coated or sustained release formulations. Suitable excipients for soft gelatine capsules are, for example, vegetable oils, waxes, fats, semi-solid and liquid polyols.

Liquid form preparations include solutions, suspensions, retention enemas, and emulsions, for example water or water/propylene glycol solutions. For parenteral injection, liquid preparations can be formulated in solution in water or water/polyethylene glycol solution.

Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents. Suitable excipients for solutions and syrups for enteral use are, for example, water, polyols, saccharose, invert sugar and glucose. Suitable excipients for injection solutions are, for example, water, saline, alcohols, polyols, e.g., polyalkylene glycols, glycerine or vegetable oils.

Compositions also may contain, in addition to the active component, colorants, flavors, stabilizers, buffers, artificial and natural sweeteners, dispersants, thickeners, solubilizing agents, preservatives, wetting agents, emulsifiers, salts for adjustment of the osmotic pressure, masking agents, antioxidants and the like.

Because the compounds of the present invention are water soluble, they can be administered intravenously in physiological saline solution (e.g., buffered to a pH of about 7.2 to 7.5). Conventional buffers such as phosphates, bicarbonates or citrates can be used in the present compositions.

Also included are solid form preparations which are intended to be converted, shortly before use, to liquid form preparations for oral administration. Such liquid forms include solutions, suspensions, and emulsions.

For preparing suppositories suitable excipients include natural and hardened oils, waxes, fatty acid glycerides, semi-liquid or liquid polyols The molten homogenous mixture is then poured into convenient sized molds, allowed to cool, and thereby to solidify.

Suitable pharmaceutical carriers, excipients and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in Examples 7–9.

The dosage can vary within wide limits and will, of course, be adjusted in each particular case to the individual requirements of the patient and the severity of the condition being treated. A typical preparation will contain from about 5% to about 95% active compound (w/w). For oral administration, a daily dosage of between about 0.01 and about 100 mg/kg body weight per day should be appropriate in monotherapy and/or in combination therapy. A preferred daily dosage is between about 0.1 and about 300 mg/kg body weight, more preferred 1 and about 100 mg/kg body weight and most preferred 1.0 and about 50 mg/kg body weight per day. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. The daily dosage can be administered as a single dosage or in divided dosages, typically between 1 and 5 dosages per day.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The nucleoside derivatives or the medicaments thereof may be used in monotherapy or combination therapy, i.e. the treatment may be in conjunction with the administration of one or more additional therapeutically active substance(s), for example, an immune system modulator such as an interferon, interleukin, tumor necrosis factor or colony stimulating factor or an anti-inflammatory agent and/or an antiviral agent. When the treatment is combination therapy, such administration may be concurrent or sequential with respect to that of the nucleoside derivatives. Concurrent administration, as used herein thus includes administration of the agents at the same time or at different times. The pharmaceutical composition may optionally contain other therapeutically active agents known in the art.

The references herein to treatment extend to prophylaxis of Hepatitis C mediated diseases as well as to the treatment of existing conditions, and that the treatment of animals includes the treatment of humans as well as other mammals. Furthermore, treatment of an Hepatitis C Virus (HCV) infection, as used herein, also includes treatment or prophylaxis of a disease or a condition associated with or mediated by Hepatitis C Virus (HCV) infection, or the clinical symptoms thereof.

The nucleoside derivatives or the medicaments thereof may be used in monotherapy or combination therapy, i.e. the treatment may be in conjunction with the administration of one or more additional therapeutically active substance(s), for example, an immune system modulator such as an interferon, interleukin, tumor necrosis factor or colony stimulating factor;another anti-viral agent or an anti-inflammatory agent. When the treatment is combination therapy, such administration may be concurrent or sequential with respect to that of the 4'-substituted nucleoside derivatives. Concurrent administration, as used herein thus includes administration of the agents at the same time or at different times.

It will be understood that references herein to treatment extend to prophylaxis as well as to the treatment of existing conditions, and that the treatment of animals includes the treatment of humans as well as other mammals. Furthermore, treatment of an Hepatitis C Virus (HCV) infection, as used herein, also includes treatment or prophylaxis of a disease or a condition associated with or mediated by Hepatitis C Virus (HCV) infection, or the clinical symptoms thereof.

PREPARATION OF POLYMORPHIC FORMS

The preparation of I was described in U.S. Ser. No. 10/167,106 which is herein incorporated by reference in its entirety.

EXAMPLE 1

Form A Polymorph

The free base (2.0 g) was dissolved in 50 mL of hot (ca. 60° C.) ethanol and a solution of 0.18 g of concentrated sulfuric acid dissolved in 2 mL of ethanol was added. The resulting slurry is aged at about 70° C. for 3 hr and then allowed to cool to rt. The precipitate was filtered (very slow filtration), washed with ethanol and dried in vacuo at about 70° C. to yield 2.1 g of the Form A polymorph of Ia. Differential scanning calorimetry indicated the onset of exothermicity at 185° C. The polymorphic form produced a x-ray scattering pattern shown in FIG. 1.

EXAMPLE 2

Form B Polymorph

The free base (0.5 g) was dissolved in 10 mL of a warm (ca. 40° C.) solution of isopropanol-water (9:1) and 1 mL of a solution of 0.875 g of concentrated sulfuric acid dissolved 10 mL of isopropanol-water (9:1) mixture was added. The resulting thick slurry is diluted with 10 mL of isopropanol-water (9:1) and 1 mL of water. The resulting slurry is aged at ambient temperature for about 2 hr and the precicpitated product was filtered, washed with isopropanol and hexanes and dried to a constant weight by application of a gentle vacuum to yield 0.56 g of the Form B polymorph of Ia. Differential scanning calorimetry indicated the onset of exothermicity at 189° C. The polymorphic form produced an x-ray scattering pattern shown in FIG. 2

EXAMPLE 3

Form C Polymorph

The free base (3.0 g) was dissolved in a solution of isopropanol (20 mL) and water (10 mL) and the solution was heated to about 60° C. A solution of dilute (ca 10%) sulfuric acid is added slowly to bring the pH to ca. 3. The resulting solution was aged to about 65–70° C. for about 2 hr while dense crystals precipitated. The slurry was cooled to ambient temperature, filtered, washed with isopropanol and dried in vacuo at about 70° C. to yield 2.8 g of the Form C polymorph of Ia. Differential scanning calorimetry indicated the onset of exothermicity at 210° C. The polymorphic form produced a x-ray scattering pattern shown in FIG. 3.

Calc'd. for $C_{18}H_{26}N_{12}O_{14}S$: C., 32.44; H 3.93; N, 25.22; S, 4.81; Found: C., 32.37; H, 3.90; N, 25.08; S, 4.80.

EXAMPLE 4

The X-ray powder diffraction patterns of samples of the polymorphic crystals were measured on a Scintag X1 powder X-ray diffractometer equipped with a sealed copper $K\alpha_1$ irradiation source. The samples were scanned from 2° to 40° 2θ at a rate of 3° per minute with incident beam slit widths of 4 and 2 microns and diffracted beam slit widths of 0.5 and 0.2 microns.

EXAMPLE 5

This example describes the method for determining the thermal properties of the Form C of Ia and 1-[4(S)-azido-2(S),3(R)-dihydroxy-4-(hydroxymethyl)-1(R)-cyclopentyl] cytosine (I) using differential scanning calorimetry (DSC). The instruments used were a Perkin-Elmer DSC-2 with heating rate of 10° per minute and the sensitivity of 5 mcal per second; or, a TA DSC 2910 scanning at 5° C./min

EXAMPLE 6

The hygroscopicity of From C of Ia at 93% relative humidity is shown in Table 1. A small amount of the polymorphic Form C crystal (about 10 mg) was weighed into a weighing bottle and placed in a chamber with controlled relative humidity for 4 weeks and the percentage of water absorbed was calculated form the weight gain. The sample was also assayed by HPLC against an external standard on a Waters 2690 HPLC at 276 nm with a Zorbax SB-Phenyl column. The mobile phase is a gradient run at 1 mL/min consisting of acetonitrile/water with 10 mM heptane sulfonic acid, 0.1% phosphoric acid in both. The gradient is run as 10% ACN to 100% in 30 min. The data was processed using Waters Millennium software version 3.2. The thermal stability also was determined at 60° C. and at 40° C./75% relative humidity. The purity of the sample was determined by assaying weighed aliquots by HPLC against an external standard. The experiments suggest that the Form C polymorph is not hygroscopic and is thermal stable at 40 and 60° C. over the duration of the assay.

EXAMPLE 7

| COMPOSITION FOR ORAL ADMINISTRATION | |
| --- | --- |
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

EXAMPLE 8

| COMPOSITION FOR ORAL ADMINISTRATION | |
| --- | --- |
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

EXAMPLE 9

| COMPOSITION FOR ORAL ADMINISTRATION | |
| --- | --- |
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 mL |
| Colorings | 0.5 mg |
| Distilled water | q.s. to 100 mL |

The ingredients are mixed to form a suspension for oral administration.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. The hemisulfate salt of 1-[4(S)-azido-2(S),3(R)-dihydroxy-4-(hydroxymethyl)-1(R)-cyclopentyl]cytosine (Ia) and solvates thereof

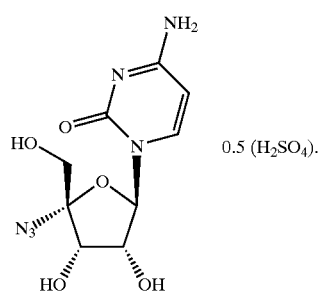

(Ia)

2. A polymorphic crystalline form (Form A) of said hemisulfate according to claim 1 with an x-ray powder diffraction trace having D-spacing essentially as shown:

| D-space | I/I$_o$ × 100 |
| --- | --- |
| 17.5556 | 26.35 |
| 10.2507 | 18.39 |
| 8.5821 | 15.58 |
| 7.2181 | 8.75 |
| 6.2309 | 62.70 |
| 5.8186 | 100 |
| 5.5808 | 30.52 |
| 4.3828 | 35.14 |
| 4.1366 | 78.45 |
| 4.1093 | 83.40 |
| 3.7211 | 18.57 |
| 3.6167 | 56.83 |
| 2.9787 | 32.98. |

3. A polymorphic crystalline form (Form B) of said hemisulfate according to claim 1 with an x-ray powder diffraction trace having D-spacing essentially as shown:

| D-space | I/I$_o$ × 100 |
| --- | --- |
| 22.8037 | 21.10 |
| 18.9103 | 13.09 |
| 16.7391 | 36.12 |
| 13.1075 | 18.80 |
| 5.7242 | 74.54 |
| 4.3696 | 100 |
| 4.1814 | 81.04 |
| 3.3481 | 36.97 |
| 3.2741 | 33.51 |
| 2.6227 | 19.75. |

4. A polymorphic crystalline form (Form C) of said hemisulfate according to claim 1 with an x-ray powder diffraction trace having D-spacing essentially as shown:

| D-space | I/I$_o$ × 100 |
| --- | --- |
| 7.7865 | 9.39 |
| 6.1199 | 5.71 |
| 6.0219 | 3.97 |
| 5.6949 | 9.68 |
| 5.4499 | 1.90 |
| 5.1928 | 13.72 |
| 4.9757 | 1.90 |
| 4.7788 | 100 |
| 3.9577 | 46.41 |
| 3.8939 | 71.89 |
| 3.7099 | 90.29 |
| 3.0178 | 26.81 |
| 2.7752 | 12.02. |

5. A process for preparing a Form A polymorph of Ia with D-spaces essentially as shown

| D-space | I/I$_o$ × 100 |
| --- | --- |
| 17.5556 | 26.35 |
| 10.2507 | 18.39 |
| 8.5821 | 15.58 |
| 7.2181 | 8.75 |
| 6.2309 | 62.70 |
| 5.8186 | 100 |
| 5.5808 | 30.52 |
| 4.3828 | 35.14 |
| 4.1366 | 78.45 |
| 4.1093 | 83.40 |
| 3.7211 | 18.57 |
| 3.6167 | 56.83 |
| 2.9787 | 32.98 | comprising crystallizing the compound (I) from an aged solution ethanol sulfuric acid.

6. A process form preparing a Form B polymorph of Ia with D-spaces essentially as shown

| D-space | I/I$_o$ × 100 |
| --- | --- |
| 22.8037 | 21.10 |
| 18.9103 | 13.09 |
| 16.7391 | 36.12 |
| 13.1075 | 18.80 |
| 5.7242 | 74.54 |
| 4.3696 | 100 |
| 4.1814 | 81.04 |
| 3.3481 | 36.97 |

-continued

| D-space | I/I$_o$ × 100 |
|---|---|
| 3.2741 | 33.51 |
| 2.6227 | 19.75 | comprising crystallizing (I) from isopropanol/water (85:15) and sulfuric acid.

7. A process form preparing a Form C polymorph of Ia with D-spaces essentially as shown

| D-space | I/I$_o$ × 100 |
|---|---|
| 7.7865 | 9.39 |
| 6.1199 | 5.71 |
| 6.0219 | 3.97 |
| 5.6949 | 9.68 |
| 5.4499 | 1.90 |
| 5.1928 | 13.72 |
| 4.9757 | 1.90 |
| 4.7788 | 100 |
| 3.9577 | 46.41 |
| 3.8939 | 71.89 |
| 3.7099 | 90.29 |
| 3.0178 | 26.81 |
| 2.7752 | 12.02 | comprising crystallizing I from isopropanol/water (60:40) in the presence of sulfuric acid.

8. A process according to claim 7 wherein the isopropanol/water is adjusted to from a pH of about 5 to a pH of about 3 with sulfuric acid.

9. A method of treating a disease mediated by the Hepatitis C Virus comprising administering to a patient in need thereof, a therapeutically effective amount of a compound according to claim 1.

10. A method according to claim 9 wherein said compound is the Form A polymorph of Ia.

11. A method according to claim 9 wherein said compound is the Form B polymorph of Ia.

12. A method according to claim 9 wherein said compound is the Form C polymorph of Ia.

13. The method according to claim 9, wherein the hemisulfate salt of compound I is delivered in a dose of between 1 and 100 mg/kg/body weight of the patient/day.

14. The method of claim 9, further comprising administering an immune sytem modulator.

15. The method of claim 9, wherein the immune system modulator is interferon or a chemically derivatized interferon.

16. A method according to claim 9 wherein the patient is a human.

17. A pharmaceutical composition comprising the hemisulfate salt Ia in admixture with at least one pharmaceutically acceptable carrier or excipient.

18. A pharmaceutical composition according to claim 17 said hemisulfate salt is the Form C polymorph.

19. A composition according to claim 17 comprising a compound of formula I and a mixture of an alcohol, water and sulfuric acid

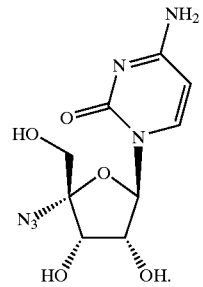

(I)

20. A composition according to claim 19 wherein the alcohol is iso-propanol.

* * * * *

UNITED STATES PATENT AND TRADEMARK OFFICE
CERTIFICATE OF CORRECTION

PATENT NO. : 6,864,244 B2
DATED : March 8, 2005
INVENTOR(S) : Terrence Joseph Connolly et al.

It is certified that error appears in the above-identified patent and that said Letters Patent is hereby corrected as shown below:

Column 13,
Line 34, "9. A method of treating a disease mediated by" should read -- . A method of treating a disease caused by --.

Signed and Sealed this

Fourth Day of October, 2005

JON W. DUDAS
*Director of the United States Patent and Trademark Office*

UNITED STATES PATENT AND TRADEMARK OFFICE
CERTIFICATE OF CORRECTION

PATENT NO. : 6,864,244 B2
APPLICATION NO. : 10/731582
DATED : March 8, 2005
INVENTOR(S) : Terrence Joseph Connolly et al.

It is certified that error appears in the above-identified patent and that said Letters Patent is hereby corrected as shown below:

Title page, item [54], in the title: replace "1-[4(S)-azido-2(S),3(R)-dihydroxy-4-(hydroxymethyl)-1(R)-cyclopentyl]cytosine hemisulfate" with --4-Amino-1-((2R,3R,4S,5R)-5-azido-3,4-dihydroxy-5-hydroxymethyl-tetrahydro-furan-2-yl)-1H-pyrimidin-2-one--

Title page, item [57], page 1 in the abstract: replace "1-[4(S)-azido-2(S),3(R)-dihydroxy-4-(hydroxymethyl)-1(R)-cyclopentyl]cytosine hemisulfate" with --4-amino-1-((2R,3R,4S,5R)-5-azido-3,4-dihydroxy-5-hydroxymethyl-tetrahydro-furan-2-yl)-1H-pyrimidin-2-one-- col. 1, lines 3-5: replace "1-[4(S)-azido-2(S),3(R)-dihydroxy-4-(hydroxymethyl)-1(R)-cyclopentyl]cytosine hemisulfate" with --4-amino-1-((2R,3R,4S,5R)-5-azido-3,4-dihydroxy-5-hydroxymethyl-tetrahydro-furan-2-yl)-1H-pyrimidin-2-one-- col. 1, lines 16-17: replace "1-[4(S)-azido-2(S),3(R)-dihydroxy-4-(hydroxymethyl)-1(R)-cyclopentyl]cytosine hemisulfate" with --4-amino-1-((2R,3R,4S,5R)-5-azido-3,4-dihydroxy-5-hydroxymethyl-tetrahydro-furan-2-yl)-1H-pyrimidin-2-one-- col. 1, lines 23-24: replace "1-[4(S)-azido-2(S),3(R)-dihydroxy-4-(hydroxymethyl)-1(R)-cyclopentyl]cytosine hemisulfate" with --4-amino-1-((2R,3R,4S,5R)-5-azido-3,4-dihydroxy-5-hydroxymethyl-tetrahydro-furan-2-yl)-1H-pyrimidin-2-one-- col. 2, lines 39-40: replace "1-[4(S)-azido-2(S),3(R)-dihydroxy-4-(hydroxymethyl)-1(R)-cyclopentyl]cytosine hemisulfate" with --4-amino-1-((2R,3R,4S,5R)-5-azido-3,4-dihydroxy-5-hydroxymethyl-tetrahydro-furan-2-yl)-1H-pyrimidin-2-one-- col. 3, lines 20-21: replace "1-[4(S)-azido-2(S),3(R)-dihydroxy-4-(hydroxymethyl)-1(R)-cyclopentyl]cytosine hemisulfate" with --4-amino-1-((2R,3R,4S,5R)-5-azido-3,4-dihydroxy-5-hydroxymethyl-tetrahydro-furan-2-yl)-1H-pyrimidin-2-one--

Signed and Sealed this

Eleventh Day of May, 2010

David J. Kappos
*Director of the United States Patent and Trademark Office*

CERTIFICATE OF CORRECTION (continued)
U.S. Pat. No. 6,864,244 B2 col. 9, lines 55-57: replace "1-[4(S)-azido-2(S),3(R)-dihydroxy-4-(hydroxymethyl)-1(R)-cyclopentyl]cytosine hemisulfate" with --4-amino-1-((2R,3R,4S,5R)-5-azido-3,4-dihydroxy-5-hydroxymethyl-tetrahydro-furan-2-yl)-1H-pyrimidin-2-one-- col. 11, lines 29-30: replace "1-[4(S)-azido-2(S),3(R)-dihydroxy-4-(hydroxymethyl)-1(R)-cyclopentyl]cytosine hemisulfate" with --4-amino-1-((2R,3R,4S,5R)-5-azida-3,4-dihydroxy-5-hydroxymethyl-tetrahydro-furan-2-yl)-1H-pyrimidin-2-one--